(12) United States Patent
Thomas

(10) Patent No.: US 10,849,520 B2
(45) Date of Patent: Dec. 1, 2020

(54) MASTOID ELECTRODE

(71) Applicant: KONINKLIJKE PHILIPS N.V., Eindhoven (NL)

(72) Inventor: Charles Thomas, Monroeville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 44 days.

(21) Appl. No.: 16/017,404

(22) Filed: Jun. 25, 2018

(65) Prior Publication Data

US 2019/0000342 A1 Jan. 3, 2019

Related U.S. Application Data

(60) Provisional application No. 62/614,725, filed on Jan. 8, 2018, provisional application No. 62/527,309, filed on Jun. 30, 2017.

(30) Foreign Application Priority Data

Aug. 23, 2017 (EP) ..................................... 17187437

(51) Int. Cl.
*A61B 5/0408* (2006.01)
*A61B 5/0478* (2006.01)
*A61B 5/00* (2006.01)
*A61B 5/0492* (2006.01)
*A61B 5/0496* (2006.01)
*A61N 1/04* (2006.01)

(52) U.S. Cl.
CPC ........ *A61B 5/04087* (2013.01); *A61B 5/0478* (2013.01); *A61B 5/0492* (2013.01); *A61B 5/0496* (2013.01); *A61B 5/4806* (2013.01); *A61B 5/6815* (2013.01); *A61B 5/6832* (2013.01); *A61N 1/0496* (2013.01); *A61B 2562/0209* (2013.01); *A61B 2562/0215* (2017.08); *A61B 2562/0217* (2017.08); *A61B 2562/164* (2013.01); *A61B 2562/227* (2013.01)

(58) Field of Classification Search
CPC ... A61B 5/0408; A61B 5/0478; A61B 5/0492; A61B 5/6814; A61B 5/6815
USPC .................................................. 600/391, 392
See application file for complete search history.

(56) References Cited

U.S. PATENT DOCUMENTS 4,354,508 A * 10/1982 Murfitt ................. A61N 1/0456
607/148
4,617,935 A * 10/1986 Cartmell ............ A61B 5/04087
600/392
4,674,511 A * 6/1987 Cartmell ............ A61B 5/04026
600/385

(Continued)

FOREIGN PATENT DOCUMENTS

WO 2013124366 A1 8/2013

*Primary Examiner* — Lee S Cohen

(57) ABSTRACT

An electrode configured to provide electrical contact with the skin of a user and configured to be positioned on or near a mastoid region of the user is provided. The electrode comprises an electrically conductive contact configured to receive electrical signals from the skin of the user, and a skin coupler that couples the contact with the skin of the user. The skin coupler comprises an adhesive layer that adhesively engages the skin. The skin coupler also comprises a base region that surrounds the contact, and at least two extension regions that extend away from the base region.

15 Claims, 5 Drawing Sheets

(56) References Cited

U.S. PATENT DOCUMENTS

| | | | | |
|---|---|---|---|---|
| 5,511,548 | A | * | 4/1996 | Riazzi ................. A61B 5/0408 600/391 |
| 7,079,884 | B1 | * | 7/2006 | Epstein .............. A61B 5/04087 600/391 |
| 9,050,451 | B2 | * | 6/2015 | Van Der Beek ....... A61N 1/048 |
| 2010/0274152 | A1 | * | 10/2010 | McPeck ............... A61B 5/0478 600/544 |
| 2014/0051946 | A1 | | 2/2014 | Arne et al. |
| 2014/0148872 | A1 | | 5/2014 | Goldwasser et al. |
| 2015/0005840 | A1 | * | 1/2015 | Pal ....................... A61N 1/0476 607/45 |
| 2016/0206225 | A1 | | 7/2016 | Todorov et al. |

* cited by examiner

MASTOID ELECTRODE

CROSS-REFERENCE TO PRIOR APPLICATIONS

This application claims the benefit of U.S. Provisional Application No. 62/527,309, filed 30 Jun. 2017, European Patent Application No. 17187437.3, filed on 23 Aug. 2017 and U.S. Provisional Application No. 62/614,725, filed 8 Jan. 2018. This application is hereby incorporated by reference herein.

BACKGROUND

1. Field

The present patent application pertains to an electrode configured to provide electrical contact with the skin of a user.

2. Description of the Related Art

For many applications in the medical field, skin electrodes are used. Electrodes generally provide electrical contact with a user's skin to transfer electrical signals between the user's skin and a medical device. Electrodes generally include a conductive layer or material that is used to transmit and receive electrical signals to and from the user. The present patent application discloses improvements over the prior art electrodes.

SUMMARY

Accordingly, it is an object of one or more embodiments of the present patent application to provide an electrode configured to provide electrical contact with the skin of a user and configured to be positioned on or near a mastoid region of the user. The electrode comprises an electrically conductive contact configured to receive electrical signals from the skin of the user, and a skin coupler that couples the contact with the skin of the user. The skin coupler comprises an adhesive layer that adhesively engages the skin. The skin coupler also comprises a base region that surrounds the contact, and at least two extension regions that extend away from the base region.

It is yet another aspect of one or more embodiments of the present patent application to provide a method for providing electrical contact with the skin of a user via an electrode. The electrode is configured to be positioned on or near a mastoid region of a user. The electrode comprises an electrically conductive contact and a skin coupler. The method comprises removably coupling, with the skin coupler, the contact with the skin of the user. The skin coupler comprises an adhesive layer that adhesively engages the skin. The skin coupler comprises a base region that surrounds the contact, and at least two extension regions that extend away from the base region. The method also comprises receiving electrical signals from the skin of the user via the contact.

It is yet another aspect of one or more embodiments to provide an electrode configured to provide electrical contact with the skin of a user and configured to be positioned on or near a mastoid region of the user. The electrode comprises means for receiving electrical signals from the skin of the user, and means for coupling the means for receiving with the skin of the user. The means for coupling comprises means for adhesively engaging the skin. The means for coupling also comprises a base region that surrounds the means for receiving, and at least two extension regions that extend away from the base region.

These and other objects, features, and characteristics of the present patent application, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the present patent application.

DETAILED DESCRIPTION OF EXEMPLARY EMBODIMENTS

Figure 1:
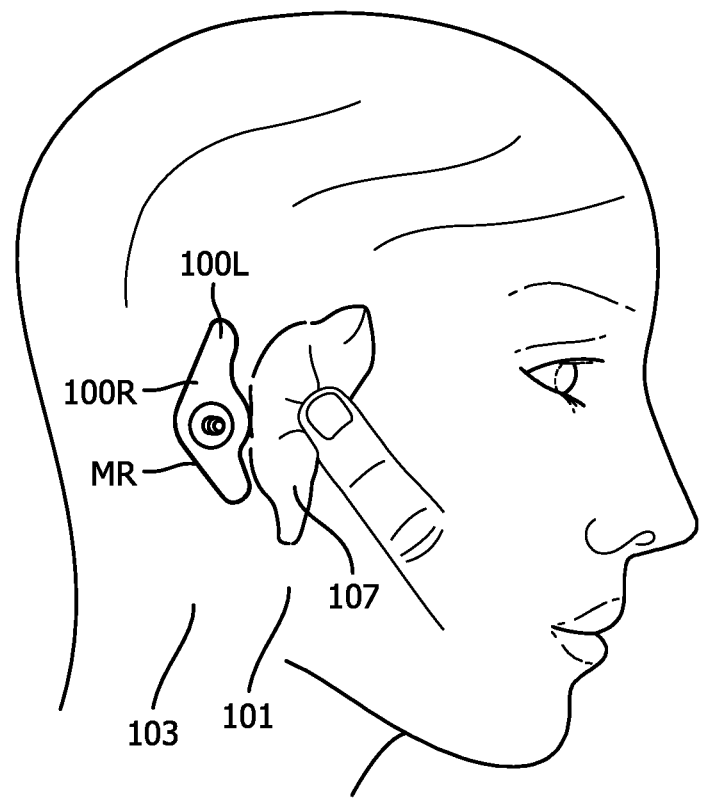
FIG. 1 shows an electrode configured to provide electrical contact with the skin of a user in accordance with an embodiment of the present patent application, wherein the electrode is positioned to reside behind, or substantially behind, an ear of the user when the electrode is worn by the user.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. As used herein, the term "or" means "and/or" unless the context clearly dictates otherwise.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

In one embodiment, referring to FIGS. 1-4, an electrode 100 is configured to provide electrical contact with the skin 101 of a user 103. Electrode 100 is configured to be positioned on or near a mastoid region MR of user 103. Electrode 100 comprises an electrically conductive contact 102 that is configured to receive electrical signals from skin 101 of user 103, and a skin coupler 104 that couples contact 102 with skin 101 of user 103. Skin coupler 104 comprises an adhesive layer 106 that adhesively engages skin 101 of user 103. Skin coupler 104 also comprises a base region 108 that surrounds contact 102, and at least two extension regions 110 that extend away from base region 108.

In one embodiment, referring to FIG. 1, region MR refers to mastoid region, located on the mastoid bone just behind the user's ear 107. In one embodiment, electrode 100 is a behind-the-ear, or mastoid electrode, which is configured to reside behind, or substantially behind, ear 107 of user 103 when electrode 100 is worn by user 103. In one embodiment, electrode 100 is configured to engage the user's head just behind ear 107. In one embodiment, electrode 100 is configured to press against the mastoid bone behind each of user's ears 107.

In one embodiment, the present patent application includes a left mastoid electrode 100L and a right mastoid electrode 100R that are each positioned on or near the mastoid bone of the respective left and right ears 107 of user 103. In one embodiment, left mastoid electrode 100L has the same structure, configuration and operation as that of right mastoid electrode 100R and that of electrode 100, and hence the structure, configuration and operation of electrode 100 will be described in detail below.

In one embodiment, electrically conductive contact 102 includes hydrogel material. The present patent application also contemplates that electrically conductive contact 102 may be formed from other materials as would be appreciated by one skilled in the art. In one embodiment, electrically conductive contact 102 includes an electrolyte material, such as a hydrogel, to provide a conductive path and fill in gaps between electrode 100 and skin 101 of user 103.

In one embodiment, skin coupler 104 may also be referred to as adhesive liner. In one embodiment, skin coupler 104 has a generally boomerang-shaped configuration. In one embodiment, skin coupler 104, including base region 108 and at least two extension regions 110, is made from a Polyethylene terephthalate (PET) material. In one embodiment, skin coupler 104 is made from a foam material. The present patent application also contemplates that skin coupler 104 may be formed from other materials as would be appreciated by one skilled in the art.

Figure 3:
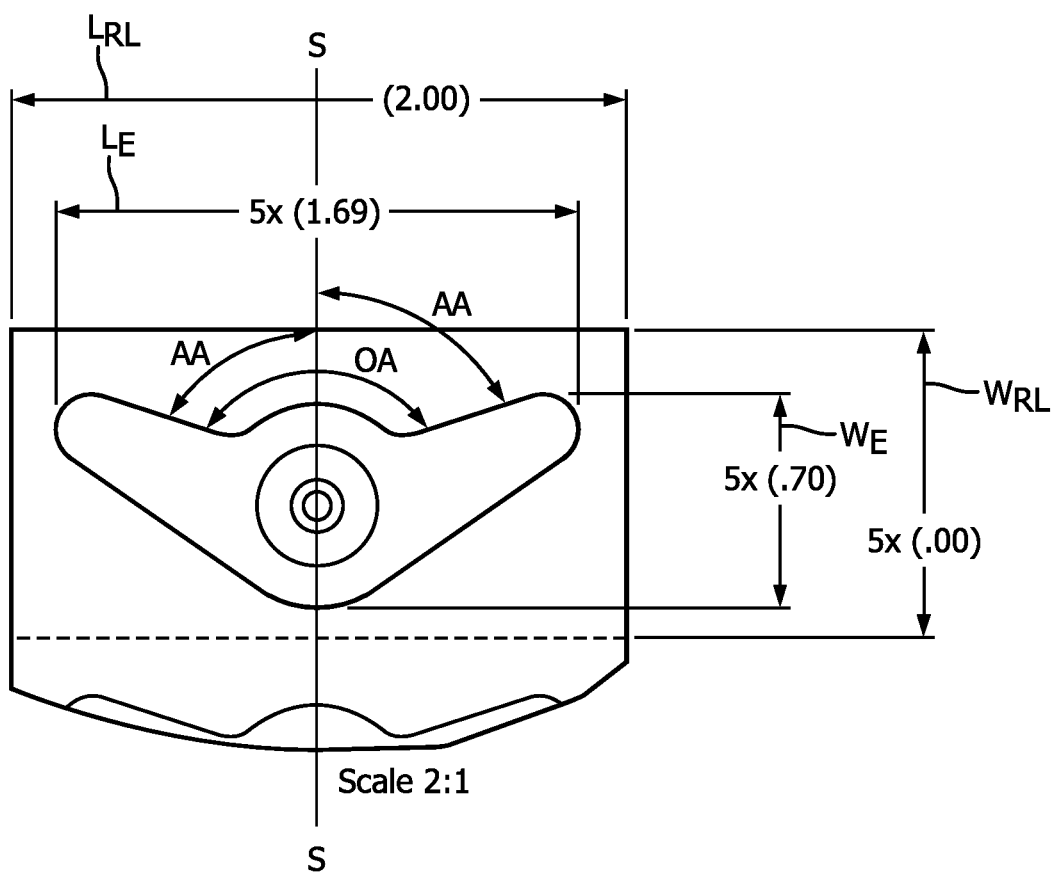
FIG. 3 shows a top elevational view of the electrode positioned on its releasable liner in accordance with an embodiment of the present patent application
Figure 4:
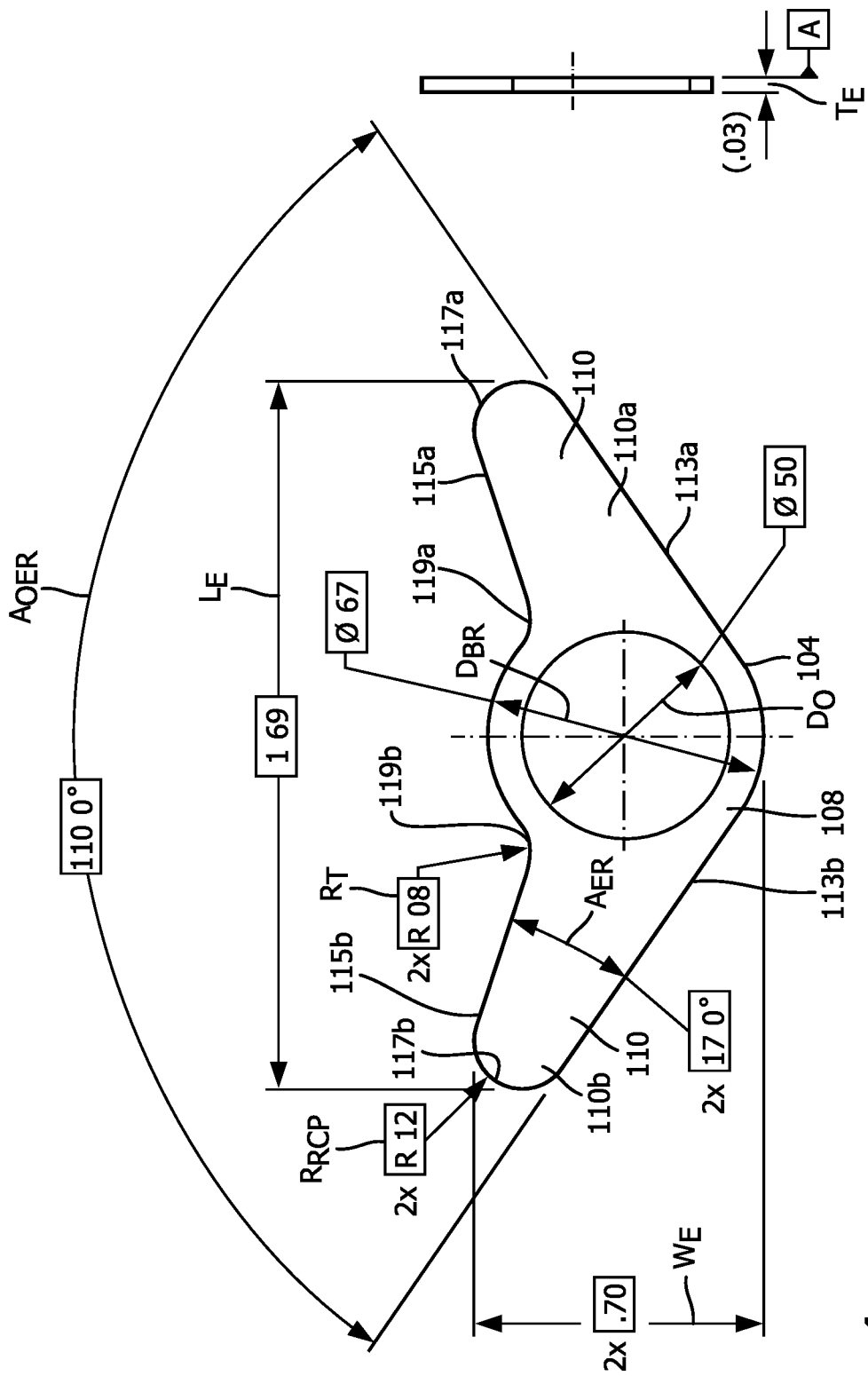
FIG. 4 shows a top elevational view of skin coupler of the electrode in accordance with an embodiment of the present patent application.

In one embodiment, as shown in FIG. 4, the diameter DBR of base region 108 of skin coupler 104 is 0.67 inches. In one embodiment, base region 108 of skin coupler 104 includes an opening 112 therein to receive and/or surround contact 102. In one embodiment, the diameter DO of opening 112 is 0.5 inches. In one embodiment, base region 108 has a rounded configuration including a convex rounded portion between extension regions 110a, 110b (spanning angle OA that is shown in FIG. 3 and discussed below). The present patent application also contemplates that base region 108 may have other shapes or configurations as would be appreciated by one skilled in the art.

In one embodiment, as shown in FIG. 3, electrode 100 includes an axis of symmetry S-S. In one embodiment, axis of symmetry S-S is the only axis of symmetry of electrode 100. In one embodiment, each of the at least two extension regions 110 make an angle AA with respect to axis of symmetry S-S. In one embodiment, the angle AA is an acute angle (i.e., less than 90 degrees). In one embodiment, the angle AA is 72 degrees. In one embodiment, the angle AA is in the range between 68 and 76 degrees. In one embodiment, at least two extension regions 110 form an obtuse angle therebetween. In one embodiment, the angle OA between the at least two extension regions 110 is 114 degrees. In one embodiment, the angle OA between the at least two extension regions 110 is in the range between 136 and 152 degrees. In one embodiment, at least two extension regions 110 form a right angle therebetween.

In one embodiment, adhesive layer 106 of skin coupler 104 is configured to cause electrode 100 to adhere to or adhesively engage with the skin of the user. In one embodiment, adhesive layer 106 is used to attach electrode 100 to the mastoid bone in a stable manner to the surrounding bone of the mastoid. In one embodiment, adhesive layer 106 is disposed on a rear/back/lower/bottom surface 153 of skin coupler 104. In one embodiment, electrode 100 may use different adhesive material types. For example, adhesive layer 106 may include skin adhesive material. In some embodiments, the adhesive for electrode 100 may include hydrocolloid or skin friendly silicone adhesive material. The present patent application also contemplates that adhesive layer 106 may have other adhesive material types as would be appreciated by one skilled in the art.

In one embodiment, skin coupler 104 may also include an adhesive layer 109 disposed on a front/upper surface 163 of skin coupler 104. In one embodiment, adhesive layer 109 is configured to cause skin coupler 104 to adhere to or adhesively engage with (lower/bottom surface of) base liner 156. In one embodiment, base liner 156 has an outer shape and configuration similar to that of skin coupler 104. In one embodiment, base liner 156 has an opening 165 therein that is configured to receive snap 167 of snap adaptor 154 therethrough.

In one embodiment, base liner 156 is made from a Polyethylene terephthalate (PET) material. In one embodiment, base liner 156 is made from a foam material. The present patent application also contemplates that base liner 156 may be formed from other materials as would be appreciated by one skilled in the art.

FIGS. 3 and 4 show various dimensions of electrode 100 in accordance with an embodiment of the present patent application. In one embodiment, the length $L_E$ of electrode 100 is 1.69 inches. In one embodiment, the length $L_E$ of electrode 100 is in the range between 1.5 and 1.9 inches. In one embodiment, the width $W_E$ of electrode 100 is 0.7 inches. In one embodiment, the width $W_E$ of electrode 100 is in the range between 0.6 and 0.8 inches. In one embodiment, the thickness $T_E$ of electrode 100 is 0.03 inches. In one embodiment, the thickness $T_E$ of electrode 100 is in the range between 0.025 and 0.035 inches.

In one embodiment, the length $L_{RL}$ of release liner 164 corresponding to one electrode 100 is 2 inches. In one embodiment, the length $L_{RL}$ of release liner 164 corresponding to one electrode 100 is in the range between 1.8 and 2.2 inches. In one embodiment, the width $W_{RL}$ of release liner 164 corresponding to one electrode 100 is 1 inches. In one embodiment, the width $W_{RL}$ of release liner 164 corresponding to one electrode 100 has no limit.

In one embodiment, referring to FIG. 4, an angle $A_{OER}$ between a surface 113a of extension region 110, 110a and a surface 113b of extension region 110, 100b is 110 degrees. In one embodiment, an angle $A_{ER}$ between the surface 113a of extension region 110, 110a and a surface 115a of extension region 110, 110a is 17 degrees. In one embodiment, an angle $A_{ER}$ between the surface 113b of extension region 110, 110b and a surface 115b of extension region 110, 110b is also 17 degrees.

In one embodiment, referring to FIG. 4, extension regions 110a, 110b of skin coupler 104 have rounded corner portions 117a, 117b, respectively. In one embodiment, each of rounded corner portions 117a, 117b is convex rounded portion. In one embodiment, the rounded corner portions 117a, 117b each have a radius of curvature $R_{RCP}$ of 0.12 inches. In one embodiment, a radius of curvature $R_T$ of transition regions 119a, 119b (between base region 108 and corresponding extension regions 110a, 110b) is 0.08 inches.

In one embodiment, the dimensions of electrode 100 and releasable liner 164 as described in the present patent application, are up to 5 percent greater than or up to 5 percent less than those described above. In one embodiment, the dimensions of electrode 100 as described in the present patent application, are up to 10 percent greater than or up to 10 percent less than those described above. In one embodiment, dimensions of electrode 100 as described in the present patent application, are up to 20 percent greater than or up to 20 percent less than those described above. In one embodiment, all the dimensions shown in FIGS. 3 and 4 are in inches. In one embodiment, all the dimensions and tolerances shown in FIGS. 3 and 4 are per ASME Y14.5 M-2009 standard.

In one embodiment, electrode 100 provides a "one-size fits all configuration" that is configured to fit most of the adult users. However, in other embodiments, electrode 100 may be manufactured in varying sizes so as to accommodate different sized users, ranging from children to adults.

Figure 2:
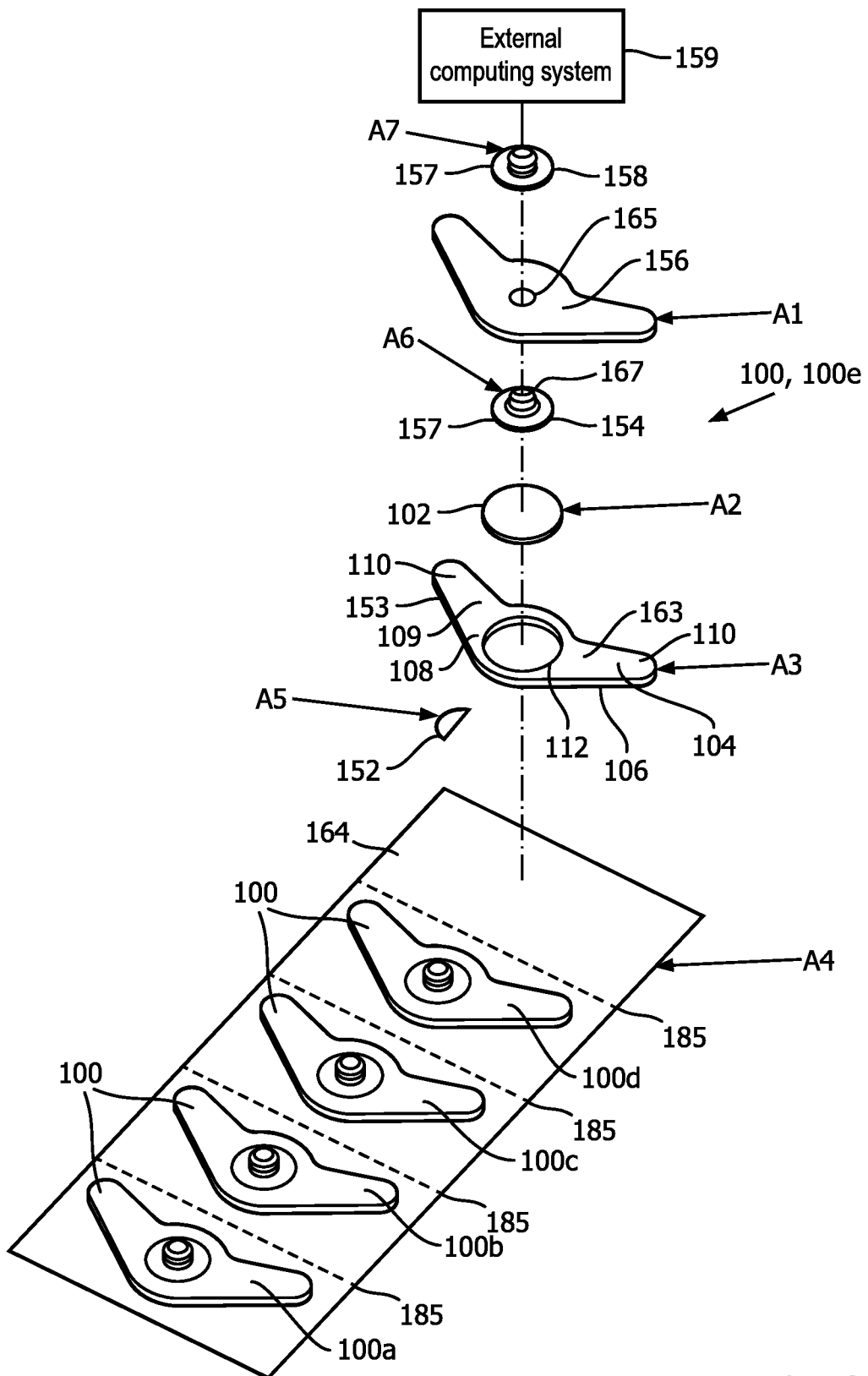
FIG. 2 shows an exploded view of the electrode in FIG. 1 and a releasable liner of such an electrode in accordance with an embodiment of the present patent application.

Referring to FIG. 2, the present patent application also includes a release tab 152 and a release liner 164. In one embodiment, release tab 152 may be attached to surface 153 of skin coupler 104. For example, when release tab 152 is used in conjunction with release liner 164, the user or a healthcare professional (e.g., nurse) can simply peel the electrode 100 away from release liner 164 by grasping release tab 152. The user can, thereafter, remove release tab 152 and position electrode 100 on or near mastoid region MR of user 103. Such release tab 152 and release liner 164 are conventional and well known.

In one embodiment, release liner 164 is made from a Polyethylene terephthalate (PET) material. In one embodiment, release tab 152 is made from urethane or polyurethane foam material. The present patent application also contemplates that release tab 152 and release liner 164 may be formed from other materials as would be appreciated by one skilled in the art.

FIG. 2 shows several identical electrodes 100, 100a, 100b, 100c, 100d, etc. as they are mounted on release liner 164 prior to use. Referring to FIG. 2, release liner 164 is in the form of a strip and is configured to accommodate one or more electrodes 100 thereon. For example, as shown in FIG. 2, release liner 164 is configured to accommodate five electrodes 100a, 100b, 100c, 100d, and 100e thereon. In one embodiment, the number of electrodes 100 accommodated on release liner 164 may vary. In one embodiment, each of electrodes 100a, 100b, 100c, 100d, 100e, etc. includes an electrically conductive contact and a skin coupler. In one embodiment, each of the electrodes 100a, 100b, 100c, 100d, 100e, etc. may be separated from the other electrode(s) by separating portions (e.g., notches, perforating lines 185). For example, a user, using the notches or perforating lines 185, may separate the strip of electrodes into individual electrodes 100a, 100b, 100c, 100d, 100e, etc. for use.

Referring to FIG. 2, electrode 100 also includes electrical coupling 157. Electrical coupling 157 facilitates coupling of electrode 100 to an external computing system 159. External computing system 159 is a system configured to deliver electrical stimulation to the user and/or monitor a physiological parameter or such of the user.

Electrical coupling 157 is electrically coupled to contact 102 such that it enables electrical signals to be received from the skin of the user. In one embodiment, additional components and/or layers of material may be disposed between electrical coupling 157 and/or contact 102. In one embodiment, electrical coupling 157 is directly coupled to contact 102. In one embodiment, electrical coupling 157 comprises one or more of a snap assembly, a magnetic assembly, a button assembly, a clip and/or clamp assembly, a wire assembly, and/or other assemblies to facilitate coupling electrode 100 to external computing system 159. For example, electrical coupling 157 includes a portion of a snap assembly for connecting one or more wires from external computing system 159 to electrode 100. In one embodiment, a portion of electrical coupling 157 may be made of a metallic material.

In one embodiment, different connection to leads may be integrated into electrode 100. For example, in one embodiment, a portion of a snap assembly is configured for connecting one or more wires from external computing system 159 to electrode 100. In one embodiment, a portion of a snap to magnetic adapter assembly is configured for connecting one or more wires from external computing system 159 to electrode 100. In one embodiment, easy to use magnetic connections may be integrated into electrode 100.

In one embodiment, electrical coupling 157 may be a male portion of a snap and a corresponding female portion of a snap may be coupled to one or more wires configured to couple electrode 100 to external computing system 159. In one embodiment, electrical coupling or snap 157 is pierced through the hydrogel material of contact 102 to establish sufficient mechanical as well as electrical contact.

In one embodiment, as shown in FIG. 2, electrical coupling 157 includes a snap adaptor 154 and a mating member 158. In one embodiment, snap adaptor 154 and mating member 158 each include a base portion and a stud member (e.g., having a diameter of 4 millimeters). In one embodiment, snap adaptor 154 is made from a stainless steel material and mating member 158 is coated from silver (Ag) or silver chloride (AgCl) material. The present patent application also contemplates that snap adaptor 154 and mating member 158 may be formed from and/or coated with other materials as would be appreciated by one skilled in the art.

In one embodiment, external computing system 159 includes one or more of processing devices (e.g., a digital processor, an analog processor, a digital circuit designed to process information, an analog circuit designed to process information, a state machine, and/or other mechanisms for electronically processing information), one or more sensors, one or more interface devices (e.g., a keypad, buttons, switches, a keyboard, knobs, levers, a display screen, a touch screen, speakers, a microphone, an indicator light, an audible alarm, a printer, a tactile feedback device, and/or other interface devices), and/or other components. In one embodiment, external computing system 159 includes one or more of measurement devices. For example, the one or more of measurement devices may be configured to obtain bioimpedance measurements, biopotential measurements, the electroencephalogram, EEG (brain-activity) measurements, Electrocardiogram, ECG (heart-activity) measurements, Galvanic Skin Response, GSR (stress) measurements, etc. For example, external computing system 159 may include a bio sensing systems used for electrocardiography (ECG), electroencephalography (EEG), electromyography (EMG), electrooculography (EOG), and/or other bio sensing applications. By way of another example, external computing system 159 may include a bio stimulation system used for transcutaneous electrical nerve stimulation (TENS), electrical muscle stimulation (EMS), neuromuscular electrical stimulation (MMES), functional electrical stimulation (FES), Galvanic Skin Response, GSR (stress), and/or other bio stimulation applications.

In one embodiment, the performance requirements of electrode 100 are as per the modified version of the ANSI/AAMI EC12 standard. In one embodiment, the electrical performance of electrode 100 is as described below. In one embodiment, the AC impedance of electrode 100 is less than or equal to 1 Kilo Ohm Average. In one embodiment, the offset voltage of electrode 100 is less than or equal to 100 milli volts. In one embodiment, the combined offset instability and internal noise of electrode 100 is less than or equal to 150 micro volts. In one embodiment, the DC voltage offset (bias current tolerance) of electrode 100 is less than or equal to 100 milli volts.

In one embodiment, the biological response of electrode 100 is per ISO 10993 standard. In one embodiment, electrode 100 remains attached to the skin of the user for two to three applications. In one embodiment, the minimum duration for each application is approximately 8 hours.

Figure 5:
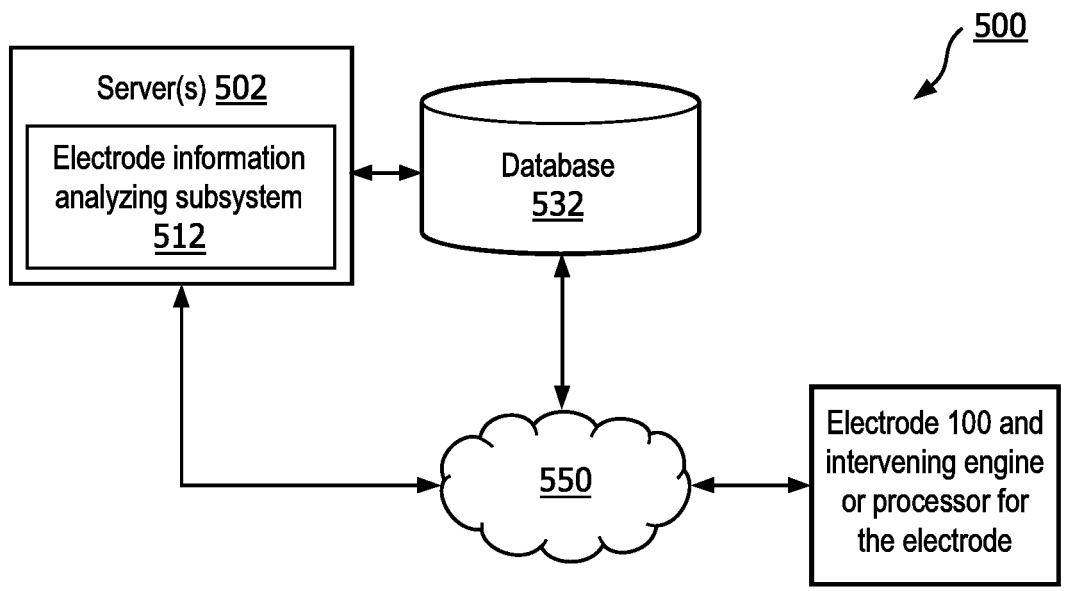
FIG. 5 shows a system having the electrode of FIGS. 1 and 2.

In one embodiment, the signals or information/data from electrode 100 may be saved into a database (e.g., database 532 in FIG. 5) and retrieved from the database as needed. As will be clear from the discussions below, in one embodiment, electrode 100 may be part of a system 500 as shown in FIG. 5. In one embodiment, system 500 includes a computer system 502 that has one or more physical processors 502 programmed with computer program instructions which, when executed cause computer system and/or one or more physical processors 502 to obtain information from one or more electrodes 100. As shown in FIG. 5, system 500 for obtaining information from one or more electrodes 100 may comprise server 502 (or multiple servers 502). Server 502 may comprise electrode data or information analyzing or processing subsystem 512, or other components or subsystems. In one embodiment, computer system (e.g., comprising server 502) obtains data/information from electrodes 100. In one embodiment, the information/data may be obtained from database 532 that is being updated in real-time by one or more electrodes 100. In one scenario, one or more electrodes 100 may provide the data/information to a computer system (e.g., comprising server 502) over a network (e.g., network 550) for processing. In one embodiment, system 500 includes an intervening engine or processor that is configured to enable the connection between electrode 100 and network 550. In one embodiment, the signals from electrode 100 are analyzed or processed by external computing system 159 or by electrode data or information analyzing or processing subsystem 512. In one embodiment, the analyzed or processed signals from electrode 100 enable the characterization of the following sleep stages: Wake, REM/light or deep sleep. In one embodiment, one or more of the above mentioned subsystems can be implemented in the same processing unit (e.g., processor or microprocessor), or can be implemented in separate processing units. It should be appreciated that the description of the functionality provided by the subsystem 512 described herein is for illustrative purposes, and is not intended to be limiting, as subsystem 512 may provide more or less functionality than is described. As another example, additional subsystems may be programmed to perform some or all of the functionality attributed herein to subsystem 512.

In one embodiment, the various computers and subsystems illustrated in FIGS. 2 and 5 may comprise one or more computing devices that are programmed to perform the functions described herein. The computing devices may include one or more electronic storages (e.g., database 532, or other electronic storages), one or more physical processors programmed with one or more computer program instructions, and/or other components. The computing devices may include communication lines or ports to enable the exchange of information with a network (e.g., network 550) or other computing platforms via wired or wireless techniques (e.g., Ethernet, fiber optics, coaxial cable, WiFi, Bluetooth, near field communication, or other communication technologies). The computing devices may include a plurality of hardware, software, and/or firmware components operating together to provide the functionality attributed herein to the servers. For example, the computing devices may be implemented by a cloud of computing platforms operating together as the computing devices.

The electronic storages may comprise non-transitory storage media that electronically stores information. The electronic storage media of the electronic storages may include one or both of system storage that is provided integrally (e.g., substantially non-removable) with the servers or removable storage that is removably connectable to the servers via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storages may store software algorithms, information determined by the processors, information received from the servers, information received from client computing platforms, or other information that enables the servers to function as described herein.

The processors may be programmed to provide information processing capabilities in system 500. As such, the processors may include one or more of a digital processor, an analog processor, or a digital circuit designed to process information, an analog circuit designed to process information, a state machine, and/or other mechanisms for electronically processing information. In one embodiment, the processors may include a plurality of processing units. These processing units may be physically located within the same device, or the processors may represent processing functionality of a plurality of devices operating in coordination. The processors may be programmed to execute computer program instructions to perform functions described herein of subsystem 512 or other subsystems. The processors may be programmed to execute computer program instructions by software; hardware; firmware; some combination of software, hardware, or firmware; and/or other mechanisms for configuring processing capabilities on the processors.

Figure 6:
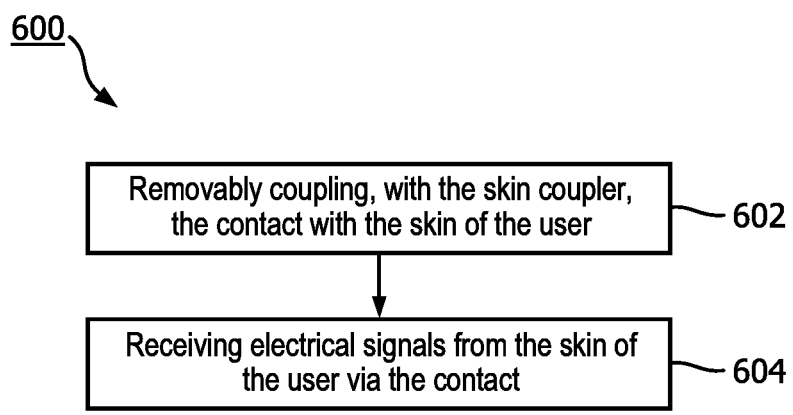
FIG. 6 shows a method for providing electrical contact with the skin of a user via an electrode of FIGS. 1 and 2.

FIG. 6 illustrates an exemplary method 600 for providing electrical contact with the skin of a user via electrode 100. Electrode 100 is configured to be positioned on or near a mastoid region of the user and includes contact 102, skin coupler 104, and/or other components. The procedures of method 600 presented herein are intended to be illustrative. In one embodiment, method 600 may be accomplished with one or more additional procedures not described, and/or without one or more of the procedures discussed. Additionally, the order in which the procedures of method 600 is illustrated in FIG. 6 and described herein is not intended to be limiting.

At a procedure 602 of method 600, contact of electrode 100 is removable coupled with the skin of the user. Procedure 602 is performed by a contact the same as or similar to contact 102 (as shown and described with respect to FIG. 2) and a skin coupler the same as or similar to skin coupler 104 (as shown and described with respect to FIG. 2). The skin coupler includes an adhesive layer that adhesively engages the skin, the skin coupler comprising a base region that surrounds the contact, and at least two extension regions that extend away from the base region. In one embodiment, the adhesive layer is the same as or similar to the adhesive layer 106 (as described with respect to FIG. 2). In one embodiment, the base region is the same as or similar to the base region 108 (as described with respect to FIG. 2). In one embodiment, the extension regions are the same as or similar to the extension regions 110 (as described with respect to FIG. 2).

At a procedure 604 of method 600, electrical signals are received from the skin of the user via the contact of the electrode. In one embodiment, procedure 604 is performed by a contact the same as or similar to contact 102 and an electrode the same as or similar to electrode 100 (as shown and described with respect to FIG. 2).

In one embodiment, method 600 may include a procedure in which coupling of the electrode to an external computing system is performed. In one embodiment, coupling of the electrode to an external computing system is facilitated via an electrical coupling the same as or similar to electrical coupling 157 (as shown and described with respect to FIG. 1).

The present patent application, thus, provides a custom design sensor/electrode for placing on the mastoid region of the human body. The electrode of the present patent application may be used for sleep monitoring devices.

The electrode of the present patent application addresses a number of issues associated with all of the designs currently on the market. Specifically, the issues including effective sensor area, maximization of adhesive region, easy to position on the primary (mastoid) region, and avoiding regions behind the ear (hairline) that may cause discomfort during removal. In addition, the design of the present patent application improves the performance specifications that exceed what is typical required by similar designs.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the present patent application has been described in detail for the purpose of illustration based on what is currently considered to be the most practical and preferred embodiments, it is to be understood that such detail is solely for that purpose and that the present patent application is not limited to the disclosed embodiments, but, on the contrary, is intended to cover modifications and equivalent arrangements that are within the spirit and scope of the appended claims. For example, it is to be understood that the present patent application contemplates that, to the extent possible, one or more features of any embodiment can be combined with one or more features of any other embodiment.

What is claimed is:

1. An electrode configured to provide electrical contact with the skin of a user and configured to be positioned on or near a mastoid region of the user, the electrode comprising:
an electrically conductive contact configured to receive electrical signals from the skin of the user; and
a skin coupler that includes an opening, wherein the opening receives the contact, wherein the skin coupler couples the contact with the skin of the user, the skin coupler comprising:
an adhesive layer that adhesively engages the skin,
a base region that surrounds the contact, and
at least two extension regions that extend away from the base region forming a first angle between the at least two extension regions on a first side of the skin coupler and a second angle on a second side of the skin coupler, the first angle being lesser than the second angle, wherein the at least two extension regions form a convex rounded portion on the first side.

2. The electrode of claim 1, further comprising an electrical coupling that is electrically coupled to the contact, wherein the electrical coupling facilitates coupling the electrode to an external computing system.

3. The electrode of claim 1, wherein the first angle is an obtuse angle in the range of about 136 and 152 degrees.

4. The electrode of claim 1, wherein the electrode comprises an axis of symmetry, and wherein each of the at least two extension regions form an acute angle with respect to the axis of symmetry.

5. The electrode of claim 1, wherein the electrically conductive contact includes an electrically conductive, hydrogel material.

6. A method for providing electrical contact with the skin of a user via an electrode, the electrode being configured to be positioned on or near a mastoid region of the user and comprising an electrically conductive contact and a skin coupler, the method comprising:
removably coupling, with the skin coupler, the contact with the skin of the user, the skin coupler including an opening, wherein the opening receives the contact, the skin coupler comprising an adhesive layer that adhesively engages the skin, the skin coupler comprising a base region that surrounds the contact, and at least two extension regions that extend away from the base region forming a first angle between the at least two extension regions on a first side of the skin coupler and a second angle on a second side of the skin coupler, the first angle being lesser than the second angle, wherein the at least two extension regions form a convex rounded portion on the first side; and
receiving electrical signals from the skin of the user via the contact.

7. The method of claim 6, further comprising coupling of the electrode to an external computing system.

8. The method of claim 6, wherein the first angle is an obtuse angle in the range of about 136 and 152 degrees.

9. The method of claim 6, wherein the electrode comprises an axis of symmetry, and wherein each of the at least two extension regions form an acute angle with respect to the axis of symmetry.

10. The method of claim 6, wherein the electrically conductive contact includes an electrically conductive, hydrogel material.

11. An electrode configured to provide electrical contact with the skin of a user and configured to be positioned on or near a mastoid region of the user, the electrode comprising:
    means for receiving electrical signals from the skin of the user; and means for coupling the means for receiving with the skin of the user, the
    means for coupling comprising means for adhesively engaging the skin, the means for coupling including an opening, wherein the opening receives the means for receiving, the means for coupling comprising a base region that surrounds the means for receiving, and at least two extension regions that extend away from the base region forming a first angle between the at least two extension regions on a first side of the means for coupling and a second angle on a second side of the means for coupling, the first angle being lesser than the second angle, wherein the at least two extension regions form a convex rounded portion on the first side.

12. The electrode of claim 11, further comprising means for facilitating coupling of the electrode to an external computing system.

13. The electrode of claim 11, wherein the first angle is an obtuse angle in the range of about 136 and 152 degrees.

14. The electrode of claim 11, wherein the electrode comprises an axis of symmetry, and wherein each of the at least two extension regions form an acute angle with respect to the axis of symmetry.

15. The electrode of claim 11, wherein the means for receiving includes an electrically conductive, hydrogel material.

* * * * *